United States Patent
Hsiao

Patent Number: 5,746,700
Date of Patent: May 5, 1998

[54] SKIN ALLERGIC TEST ASSEMBLY

[76] Inventor: Ray-Ling Hsiao, 4F, No. 12,Alley 15,Lane 175,Ho-Ping East Rd., 2nd Sec., Taipei, Taiwan

[21] Appl. No.: 598,235

[22] Filed: Feb. 7, 1996

[51] Int. Cl.[6] ..................................................... A61B 5/00
[52] U.S. Cl. .............................................................. 600/556
[58] Field of Search ........................... 128/743; 604/43, 604/46

[56] References Cited

U.S. PATENT DOCUMENTS

| | | | |
|---|---|---|---|
| 4,237,906 | 12/1980 | Havstad et al. | 128/743 |
| 4,802,493 | 2/1989 | Maganias | 128/743 |
| 5,538,134 | 7/1996 | Pitesky | 128/743 |
| 5,551,441 | 9/1996 | Pitesky | 128/743 |

*Primary Examiner*—Max Hindenburg
*Attorney, Agent, or Firm*—W. Wayne Liauh

[57] ABSTRACT

A skin allergic test assembly comprises at least a skin puncture test bar (3), a tray (50), a antigen-containing cup (9), and a multiple-test-bar access device (19). The skin puncture test bar, which generally comprises a finger grip (4), an elongate stem (6), and a plurality of punctures (12), is characterized in that the elongate stem is provided with a concave surface (10) to which the punctures are attached, so that the penetration made by the skin puncture test bar will have a limited penetration depth to avoid the penetration through of the epidermis layer of the skin of a patient due to the outer edge of the concave surface. By using the skin puncture test bar of the present invention, a good and accurate skin test result can be obtained. The multiple-test-bar access device, which is employed to facilitate a skin allergic test in which various specific kinds of antigen solution are required, generally comprises a main frame (18), a first clamping plate (24), a second clamping plate (26), and an outer panel (28). The first clamping plate and the second clamping plate are furnished respectively with a plurality of semicircular-shaped cuts (34a) (34b) while the outer panel is furnished with two parallel rows of holes (38), where each hole is provided with an arcuate ridge (40) at its outer edge for cooperating with each semicircular-shaped correspondingly cut to form multiple gripping holes therebetween for taking multiple skin puncture test bars simultaneously.

6 Claims, 14 Drawing Sheets

SKIN ALLERGIC TEST ASSEMBLY

FIELD OF INVENTION

The present invention relates to a skin allergic test assembly, and, more particularly, to an improved skin puncture test bar by which a limited penetration can be made, and a multiple-test-bar access device for holding multiple skin puncture test bars simultaneously for facilitating a skin allergic test.

BACKGROUND OF INVENTION

Figure 1:
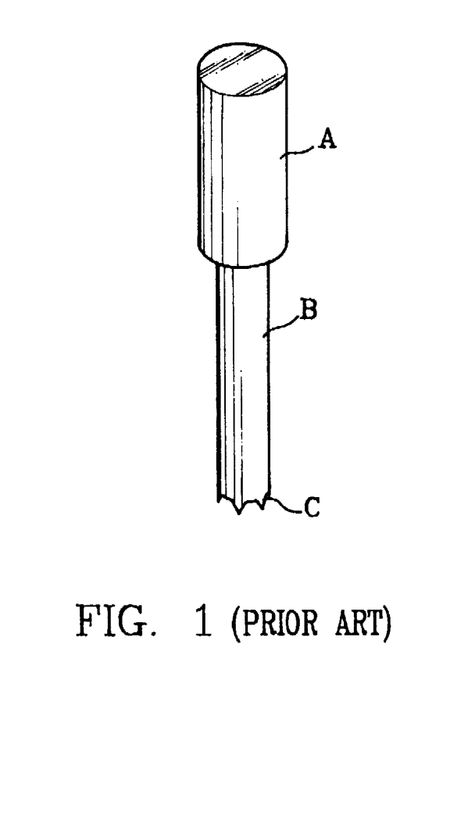
FIG. 1 shows a conventional skin puncture test device of prior art.
Figure 2:
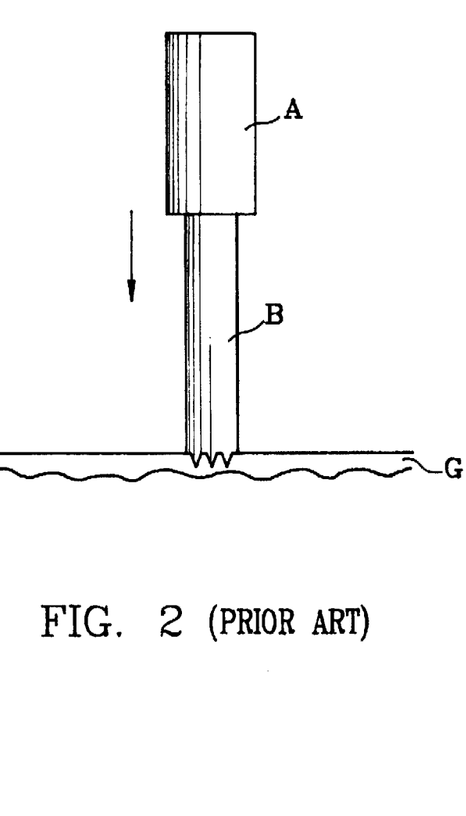
FIG. 2 is a schematic diagram showing how a skin puncture test bar of prior art to be operated.

For a skin allergic test, the allergic test conducted by a puncture test device is one of the most popular methods at present. A conventional puncture device, as shown in FIG. 1, generally comprises a finger grip (A), an elongate stem (B) extending therefrom, and a plurality of punctures (C) attached to the end of the elongate stem (B). In use, the conventional puncture test device, as other skin allergic test devices of prior art will be forced into the skin (G) of a patient (referring to FIG. 2) by its punctures (C). A properly performed skin allergic test will leave a visible scarification. The scarification will correspond to the punctures (C) of the test device. Then, an adequate amount of antigen solution carried by punctures (C) due to the capillary phenomenon may be given to the test site of the patient so as to create a complete reaction thereon, the result of which will be properly interpreted about 20 minutes after the specific antigen solution has been provided.

Although various conventional skin allergic test devices have provided the practitioners or technicians in the art with a convenient way in performing a skin allergic test, yet none of the conventional test device can be used easily by a person with ordinary skill in the art, since the skin allergic test performed by a puncture test device, should meet the following condition in order to obtain a good and an accurate interpretation for the test result:

(1) the punctures of a skin allergic test device should not be penetrated through the epidermis layer of the skin of a patient while conducting the skin allergic test, as indicated in *Allergic Principles And Practice*, 3rd edition, p423–425, by Elliott et al.;

(2) the antigen solution carried by the punctures of a skin allergic device should be adequate in order to allow the reaction on the test site to occur completely; and (3) the skin allergic test can be readily performed by anyone with ordinary skill to create a reproducible test result.

However, the epidermis of human being is extremely thin, it is therefore very likely for the epidermis of the skin to be penetrated by the punctures of the test devices. As a result, the conventional skin puncture device, like other skin test devices of prior art, should be performed by a skillful practitioner or technician in the art.

Figure 3:
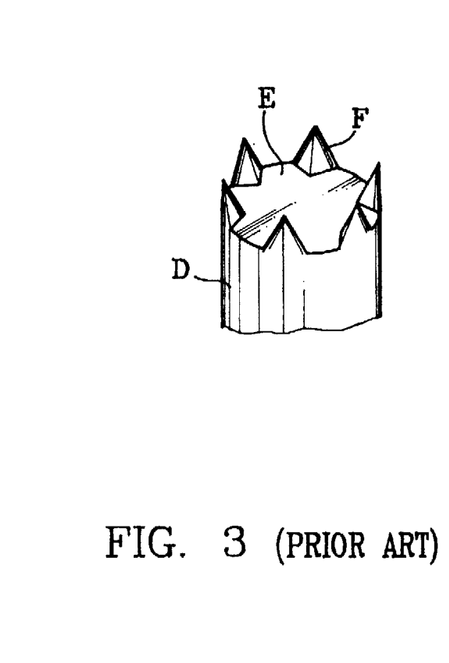
FIG. 3 shows another skin puncture test bar of prior art in which the punctures is formed at a flat end surface which is act as a stop.
Figure 4:
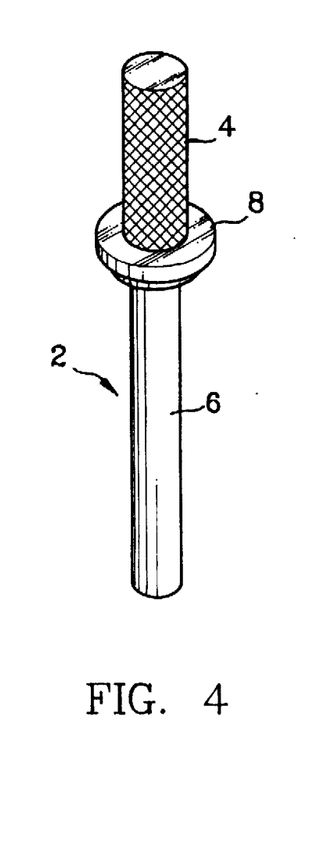
FIG. 4 is a perspective view of skin puncture test bar of the present invention.
Figure 5:
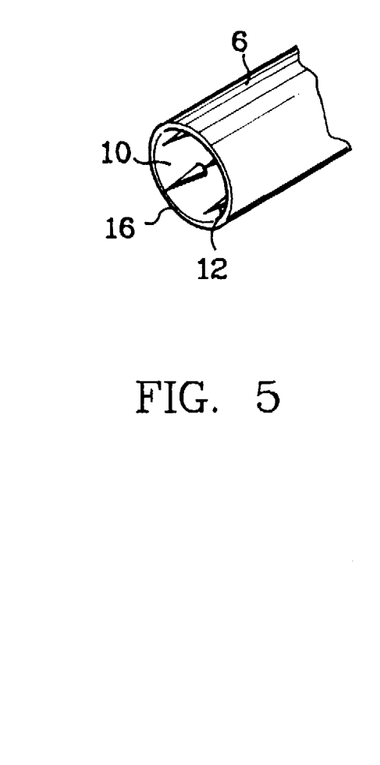
FIG. 5 shows the improved aspect regarding the skin puncture test bar of the present invention.
Figure 6A:
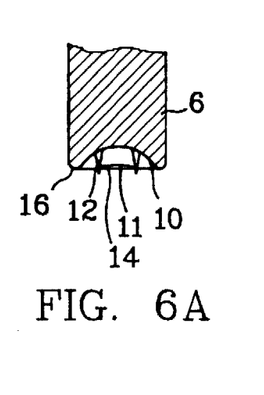
FIG. 6A is a loginitudinal sectional view of the skin puncture test bar as shown FIG. 5.
Figure 6B:
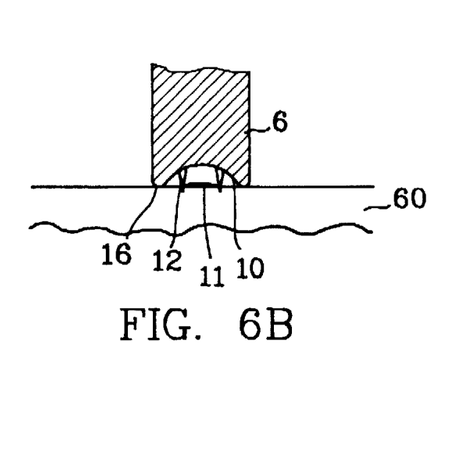
FIG. 6B id the same longitudinal sectional view as shown in FIG. 6A, execpt that it also shows the addition feature of having the skin puncture test bar applied on a human's epidermis layer.

Referring to FIG. 3, U.S. Pat. No. 4,237,906 to Havstad et al. discloses an applicator or skin puncture test device in which a flat end surface (E) is provided at the end of an elongate stem (D), and a plurality of pointed projection (F) are attached to the flat end surface. Therefore, the flat end surface (E) can be act as a stop when forcing the applicator into the skin of a patent.

Although the flat end surface (E) can be act as a top to limit the depth of penetration, it is very difficult for such an applicator to be manufactured in that way since the projection (F) of the applicator must be made and extends from the flat end surface (E) to have an extremely short length of approximate 0.1–0.5 mm. Even though such manufacturing difficulty can be overcome, it is difficult for the projection (F) of an extremely short length about 0.1–0.5 mm to carry an adequate amount of antigen solution therebetween for conducting a skin allergic test due to its extremely short length.

Accordingly, the primary objective of the present invention is to provide an improved skin puncture test bar which permits the skin of a patient to be penetrated only to a limited extent by the punctures thereof in order to avoid the penetration through of the epidermis of the skin, and which enables the punctures thereof to carry an adequate antigen solution to the test site of a patient so as to obtain a good and accurate test result, therefore making the skin allergic test to be more easily conducted by persons with ordinary skills and making the test result to be reproducible.

Further, the present invention also provides a multiple-test-bar access device for holding multiple skin test bars simultaneously to facilitate a skin allergic test with various kinds of antigen solution so that the skin allergic test may be completed immediately simply by forcing the multiple-test-bar access device onto the test site of a patient.

Still further, the present invention also provides a skin allergic test assembly, which comprises a plurality of skin puncture test bars and the multiple-test-bar access device of the present invention, a tray, and a plurality of antigen-containing cups. Regarding a skin allergic test which requires various specific kinds of antigen solution, the assembly may be operated in a one-by-one manner in which the skin puncture test bars each with a specific antigen solution can be brought to force against the skin of a patent sequentially or simultaneously manner in which all the skin puncture test bars involved in the skin allergic test will be completed immediately by pressing the multiple-test-bar access device onto the skin of a patient. The further objectives and objectives regarding this invention will become apparent from a consideration of the ensuing descriptions and drawings.

SUMMARY OF INVENTION

The primary objective of the present invention is to provide an improved skin puncture test bar, which comprises a finger grip, a cover, an elongated stem extending therefrom, and a plurality of punctures; wherein the end of the elongate stem is provided with a concave surface. The punctures are furnished on the concave surface in such a manner that the punctures extend directly from the concave surface substantially parallel to the elongate stem to project out of the outer edge of the concave surface at a predetermined length less than the thickness of the human epedermis, particularly between about 0.1 mm to about 0.5 mm, so that the outer edge of the concave surface may act as a stop to avoid the penetration through of the epidermis layer of the skin when conducting a skin allergic test. Further, the puncture can provide an adequate amount of antigen solution to the skin of a patient to allow the test reaction on the test site to occur completely so as to obtain a good and accurate skin test result.

Another objective of the present invention is to provide a multiple-test-bar access device for holding multiple skin test bars simultaneously, which comprises a main frame, a first clamping plate, a second clamping plate, and an outer panel; wherein said main frame has a handle, a slot, and a bottom opening; said first clamping plate is formed with a plurality of semicircular-shaped cuts along a longitudinal edge thereof and said first clamping plate is furnished with a box at the other longitudinal edge thereof for housing a spring means therein, the height of said box being greater than the depth of said slot of said frame; said second clamping plate is formed with a plurality of semicircular-shaped cuts along a longitudinal edge thereof and said second clamping plate is furnished a mating box at the other longitudinal edge thereof, where the height of said mating box is greater than the depth of said slot of said main frame; said outer panel is formed with two parallel rows of holes, each hole corresponding to each semicircular-shaped cut of said first and second plates and each hole being furnished with an arcuate ridge at its outer edge for cooperating with each semicircular-shaped cut; said box and said mating box are assembled together to form an elastic and relatively-movable integral enclosure in which said spring mean is housed, and said enclosure is assembled into said slot and extends out of said slot to form a switch portion thereon, so that said spring means can exert an elastic force on each inner surface of said box and said mating box to have said clamping plate and said clamping plate capable of providing an outward force, and said box and said mating box can be moved toward each other as pressing said switch portion; said outer panel is placed to cover said bottom opening of said main frame and abut both of said first clamping plate and said second clamping plate where each hole of said outer panel is located to correspond to each semicircular-shaped cut of said first and second plates so that each arcuate ridge associated thereat can cooperate with each semicircular-shaped cut to form a gripping hole therebetween which is coaxial with each corresponding hole of the outer panel, where the diameter of each said gripping hole is somewhat smaller than that of each skin test bar in normal state while said hole of said outer panel is larger than the finger grip of each skin puncture bar; when pressing said switch portion, said first clamping plate and said second clamping plate will move toward each other; thereby making all the gripping holes get larger simultaneously so as to accommodate the multiple skin puncture test bars simultaneously; when releasing the pressing force, said spring means will enable said first clamping plate and said second clamping plate to clamp the multiple skin puncture test bars by means of said semicircular-shaped cut and said cooperating arcuate ridge so as to take the multiple skin puncture test bars simultaneously.

Still another objective of the present invention is to provide a skin allergic test assembly for facilitating a skin allergic test, which comprises a plurality of skin puncture test bars, a plurality of antigen-containing cups, a tray, and a multiple-test-bar access device; wherein each said skin puncture test bar has a cover, an elongate stem extending therefrom and having a concave surface at the end thereof, and a plurality of punctures, said punctures provided on said concave surface in such a manner that said punctures extend directly from said concave surface substantially parallel to said elongate stem to project out of the outer edge of said concave surface at a predetermined length less than the thickness of the human epidermis to prevent said punctures from penetrating into the epidermis layer of the skin of a patient in order to obtain a good and accurate skin allergic test result; said tray has two parallel rows of tray holes formed thereon for holding said antigen-containing cup; the multiple-test-bar access device, which can hold skin puncture test bars simultaneously, has a main frame, a first clamping plate, a second clamping plate, and an outer panel, where said main frame has a handle for being held by users' fingers, a slot, and a bottom opening; said first clamping plate is formed with a plurality of semicircular-shaped cuts along a longitudinal edge thereof and furnished with a box at the other longitudinal edge thereof for housing a spring means therein, the height of said box being greater than the depth of said slot of said main frame; said second clamping plate is formed with a plurality of semicircular-shaped cuts and furnished a mating box at the other longitudinal edge thereof, the height of said mating box being greater than the depth of said slot of said main frame; said outer panel is formed with two parallel rows of holes thereon, each said hole aligned to correspond to each said semicircular-shaped cut of said first and second clamping plate as well as each said tray hole on said tray, each said hole furnished with an arcuate ridge at its outer edge for cooperating with each said semicircular-shaped cut correspondingly; said box and said mating box are assembled together to form an elastic and relatively-movable integral enclosure in which said spring means is housed, and said enclosure is assembled into said slot and extends out of said slot to form a switch portion thereabove, so that said spring means can exert an elastic force on each inner surface of said box and said mating box to have said first clamping plate and said clamping plate capable of providing on outward force, and said box and said mating box can be moved toward each other as pressing said switch portion; said outer panel is placed to cover said bottom opening of said main frame and abut both of said first clamping plate and said second clamping plate, where each said hole of said outer panel is located to correspond to each said semicircular-shaped cut of said first clamping plate and said second clamping plate so that each said arcuate ridge can cooperate with each semicircular-shaped cut correspondingly to form multiple gripping holes therebetween, each gripping hole being coaxial with its corresponding hole of said outer panel, the diameter of said gripping hole being somewhat smaller than that the finger grip of each skin puncture test bar in normal state; when pressing said switch portion, said first clamping plate and said second clamping plate will move toward each other, thereby making all the gripping holes get larger simultaneously so as to accommodate the multiple skin puncture test bars simultaneously; when releasing the pressing force, said spring means can enable said first clamping plate and said second clamping plate to clamp the multiple skin puncture test bars by means of said arcuate ridges and said semicircular-shaped cuts so as to take the multiple skin puncture test bars simultaneously.

REFERENCE NUMERALS IN DRAWINGS

| | |
|---|---|
| (2) | skin allergic test bar |
| (4) | finger grip |
| (6) | elongate stem |
| (8) | cover |
| (9) | antigen-containing cup |
| (10) | concave surface |
| (11) | antigen solution |
| (12) | punctures |
| (13) | ring |
| (14) | fictitious flat plane |
| (16) | outer edge |
| (18) (18a) | main frame |
| (19) | multiple-test-bar access device |
| (20) | handle |
| (22) | slot |
| (23) | bottom opening |
| (24) (24a) | first clamping plate |
| (26) (26b) | second clamping plate |
| (28) (28a) | outer panel |
| (30) | box |
| (32) | spring means |
| (34a) | semicircular- shaped cut of first clamping plate |
| (34b) | semicircular- shaped cut of second clamping plate |
| (36) | mating box |
| (38) | hole |
| (40) | arcuate ridge |
| (42) | switch portion |
| (50) | tray |
| (52) | tray hole |
| (60) | epidermis layer |
| (80a) (80b) | wave-like side |
| (82) | frame hole |
| (100a) (100b) | wave-like edge of outer panel |
| (102) | adjacent space |
| (104) | projection |

DETAILED DESCRIPTION OF INVENTION

Referring to FIGS. 4, 5, 6A and 6B, a skin puncture test bar (2) or a skin allergic test bar of the present invention, which may be made from plastic materials, comprise a finger grip (4), an elongate stem (6) extending therefrom, and a cover (8) furnished between the finger grip (4) and the elongate stem (6). The end of the elongate stem (6) is provided with a concave surface (10) on which a plurality of punctures (12) are furnished. Particularly, the punctures (12), which extends directly from the concave surface (10) substantially parallel to the elongate stem (6), are designed to project out of the fictitious flat plane (14) which is imaginarily formed by the outer edge (16) of the concave surface (10) at approximately 0.1–0.5 mm which is somewhat smaller than the thickness of the epidermis layer of the skin of human being. Therefore, the depth of penetration made by the skin puncture test bar (2) will be limited due to the outer edge (16) of the concave surface (10) which is act as a stop.

Referring again to FIG. 4, 5, 6A and 6B, the punctures (12) of the present invention are designed and extends directly from the concave surface (10) to have an adequate length about 2 mm so as to carry an adequate amount of antigen solution therebetween by capillary action, since the punctures each have an adequate length so as to carry enough antigen solution into the gap formed by the punctures, which will in turn be loaded into the epidermis layer (60) of a patient. For a skin allergic test an adequate amount of antigen solution have also been regarded as a significant factor for obtaining an accurate interpretation of the skin allergic test result.

Figure 7:
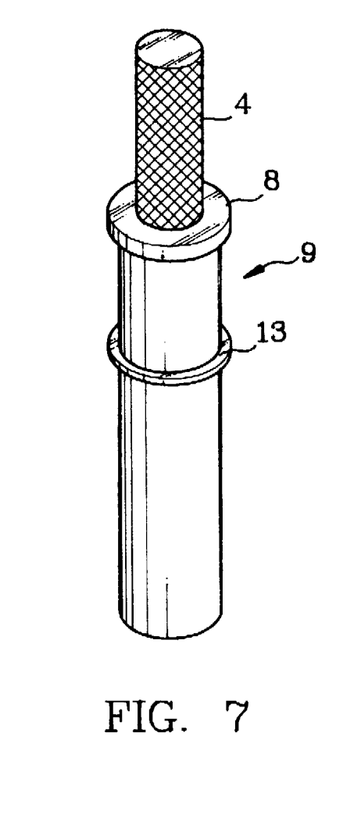
FIG. 7 shows a antigen-containing cup where a skin puncture test bar is brought to mate therewith.

Referring next to FIG. 7, the skin puncture test bar (2) of the present invention may be brought in place with an antigen-containing cup (9) whenever a skin allergic test is not in demand. As shown in the figure, the punctures (12) of the skin test bar (2) will be wetted by the antigen solution (11) in the cup (9), such an aspect regarding the skin test bar (2) will therefore facilitate the next skin allergic test. Also, as shown in the figure, we note that the cover (8) of the skin test bar (2) is placed over the mouth of the antigen-containing cup (2), such feature regarding the cover (8) will prevent foreign materials from entering the antigen-containing cup.

Figure 8:
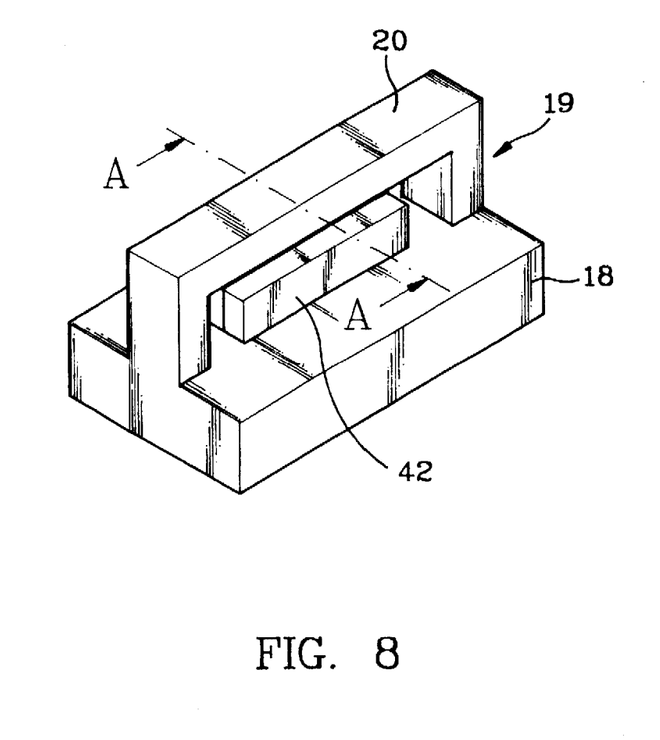
FIG. 8 is a perspective view of a multiple-test-bar access device of the first embodiment.
Figure 9:
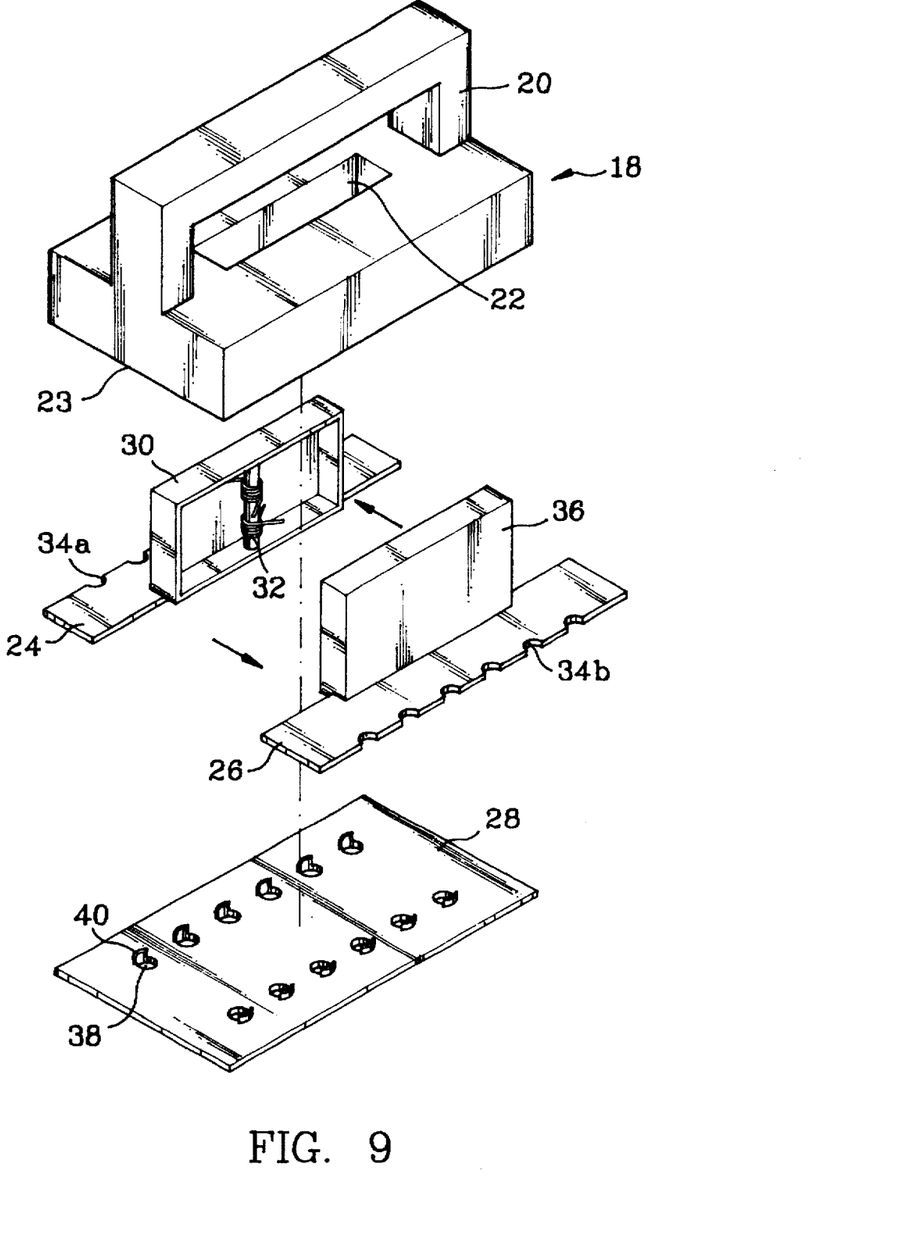
FIG. 9 is an exploded view regarding the multiple-test-bar access device of the first embodiment.

Further, in order to allow a skin allergic test to be conducted more conveniently, a multiple-test-bar access device (19) is disclosed herein for cooperating with the skin allergic test bar of the present invention. As shown in FIG. 8–9, the multiple-test-bar access device (19), which can access multiple skin allergic test bars of any commercial types simultaneously, generally comprises a main frame (18), a first clamping plate (24), a second clamping plate (26), and an outer panel (28). The main frame (18) has a handle (20) for being held by fingers, a slot (22), and a bottom opening (23). The first clamping plate (24) is formed with a plurality of semicircular-shaped cuts (34a) along a longitudinal edge thereof and is furnished with a box at the other longitudinal edge thereof for housing a spring means (32) therein. The height of the box is greater than the depth of the slot (22) of the main frame (18) The second clamping plate (26) is formed with a plurality of semicircular-shaped cuts (34b) along a longitudinal edge thereof and is furnished with a mating box (36) at the other longitudinal edge thereof. The height of the mating box (36) is greater than the depth of the slot (22). The mating box (36) attached at the second clamping plate (26) is somewhat greater than the box (30) attached at the first clamping plate (24) for mating with the box (30). The outer panel (28) is formed with two parallel rows of holes (38) thereon, the hole each are furnished with arcuate ridges (40) respectively at their outer edges for cooperating semicircular-shaped cuts (34a), (34b) of the first and second clamping plates correspondingly.

Figure 10:
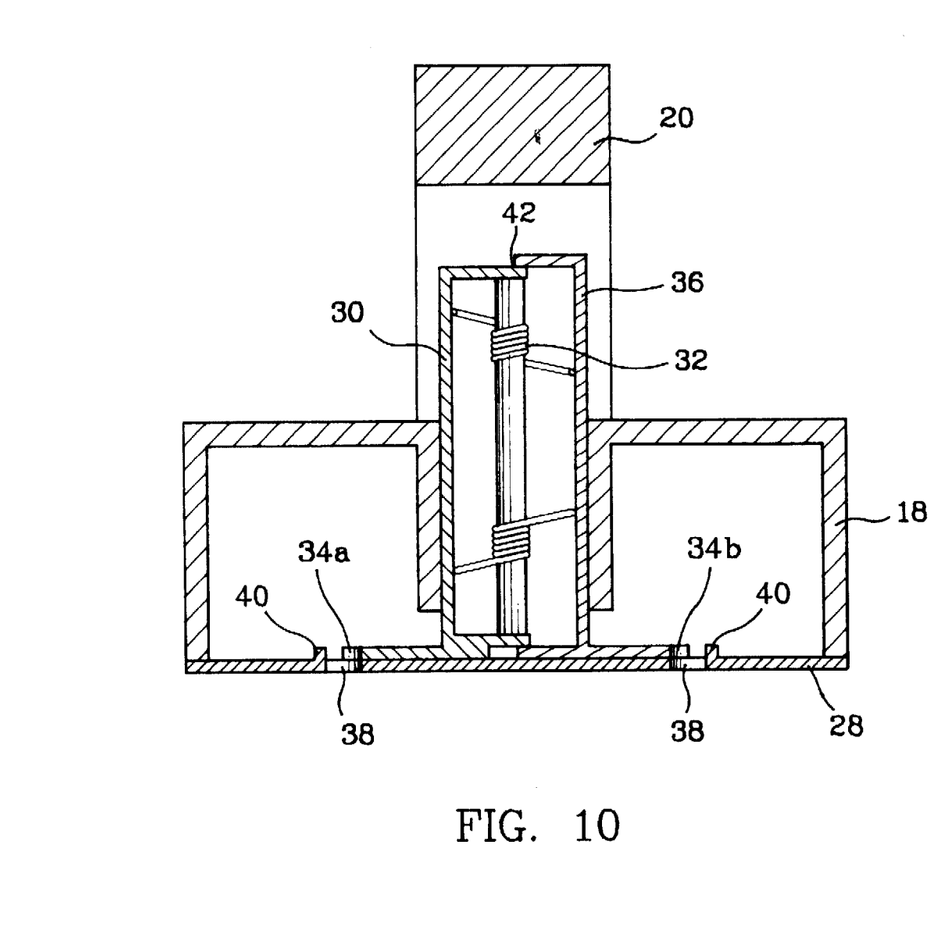
FIG. 10 is a sectional view taken along A—A line of FIG. 8, which shows the combination aspect of the multiple-test-bar access device of the first embodiment.

Referring to FIG. 10 is a sectional view taken along A—A line of FIG. 8, which shows the combination aspect of all comprising elements involved in the multiple-test-bar access device. All above-mentioned elements regarding the multiple-test-bar access device (19) are taken to assembled together in such a manner that the box (30) at the first clamping plate (24) is taken to assemble with the mating box (36) at the second clamping plate to form an elastic and relatively-movable integral enclosure in which the spring means (32) is housed. The enclosure, the height of which is greater than the depth of the slot (22) of the main frame (18), is taken to assemble into the slot (22) of the main frame and extends out of the slot to form a switch portion (42) thereabove. The spring means (32) can therefore exert an elastic force on each inner surface of the box (30) and the mating box (36) so as to have the first clamping plate (24) and the second clamping plate (26) capable of providing an outward force, and the box (30) and the mating box (36) of the enclosure can be moved toward each other when pressing the switch portion so as to accommodate multiple skin test bars simultaneously, the performance with regard to which will become apparent after a reading of the following description.

Figure 11:
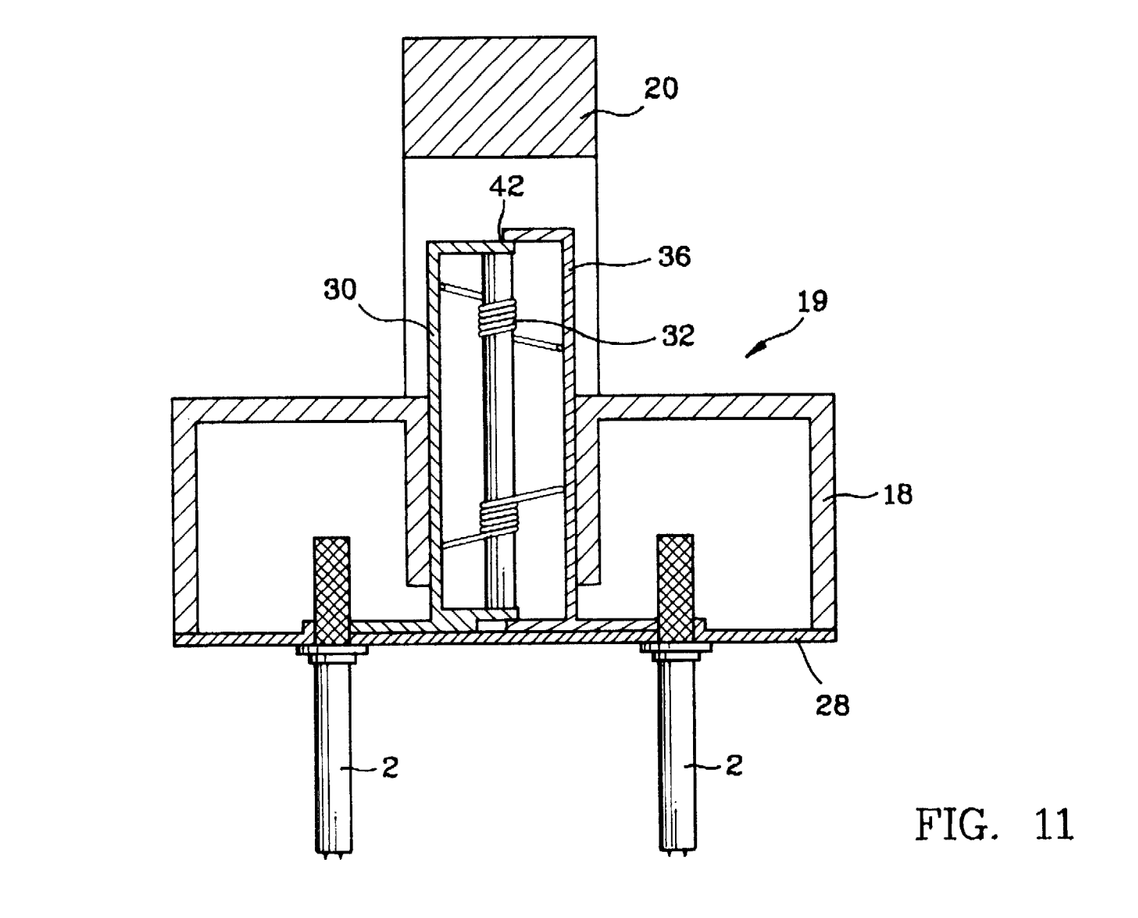
FIG. 11 is a sectional view similar to FIG. 10 in which multiple skin puncture test device (at least two) being held by the multiple-test-bar access device of the first embodiment is shown.
Figure 12:
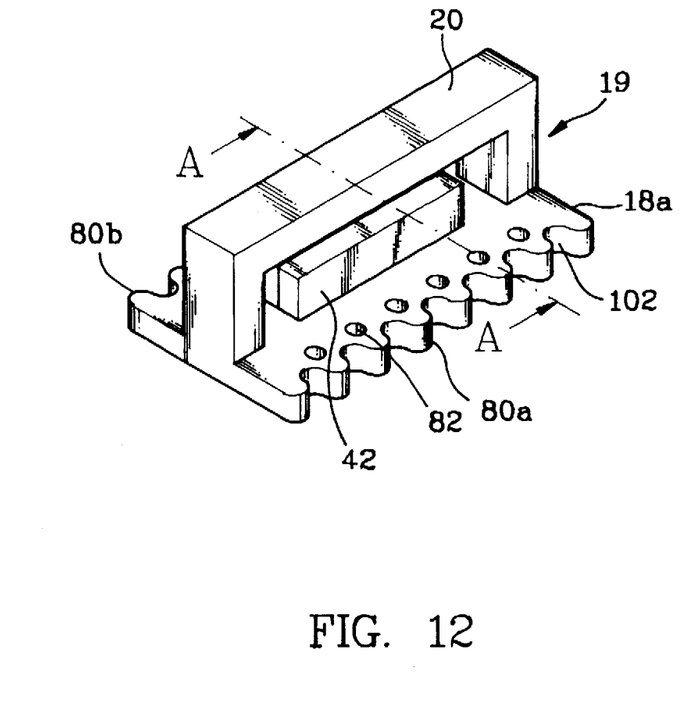
FIG. 12 is a perspective view of a multiple-test-bar access device of the second embodiment.
Figure 13:
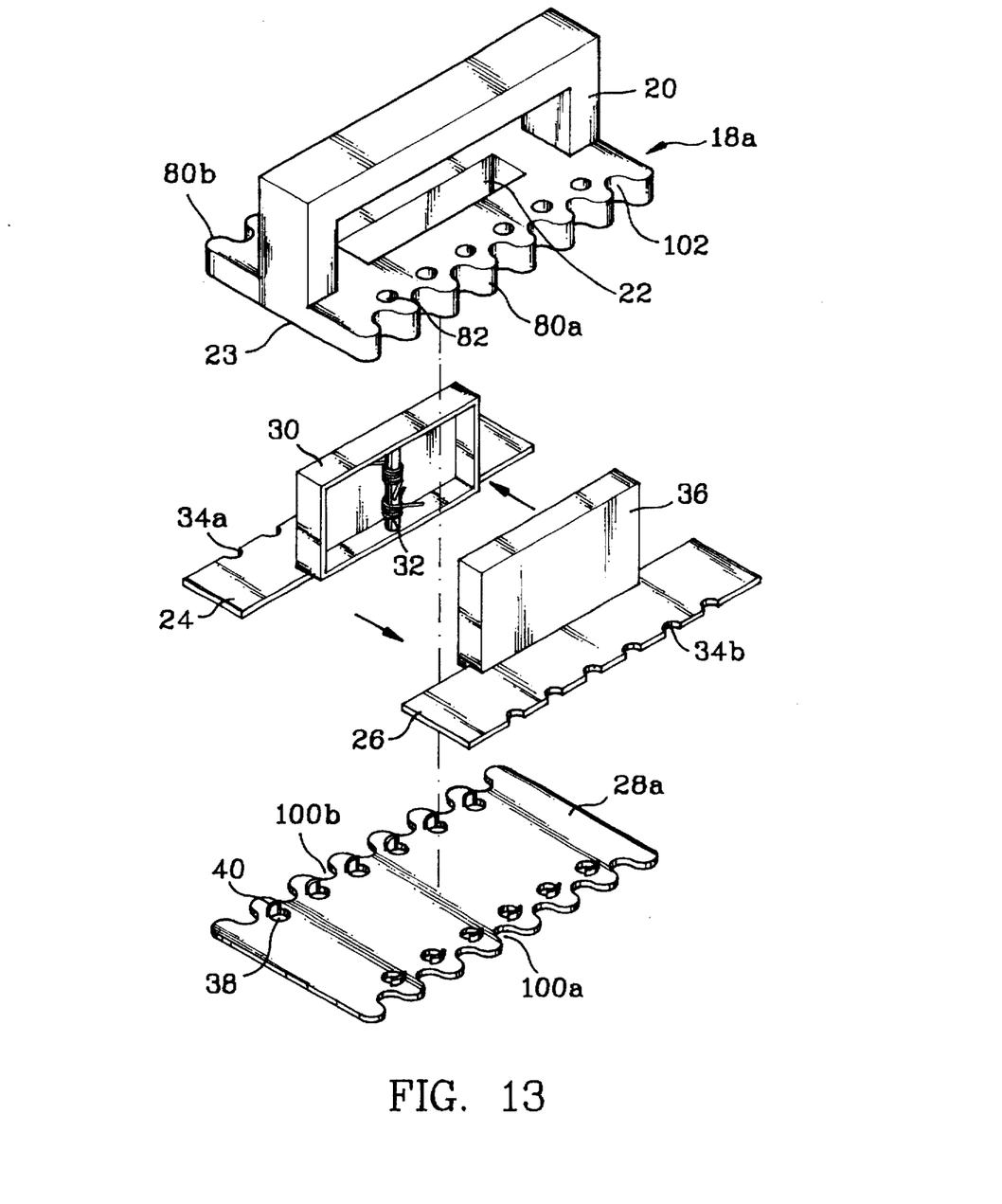
FIG. 13 is an exploded view regarding the multiple-test-bar access device of the second embodiment.
Figure 14:
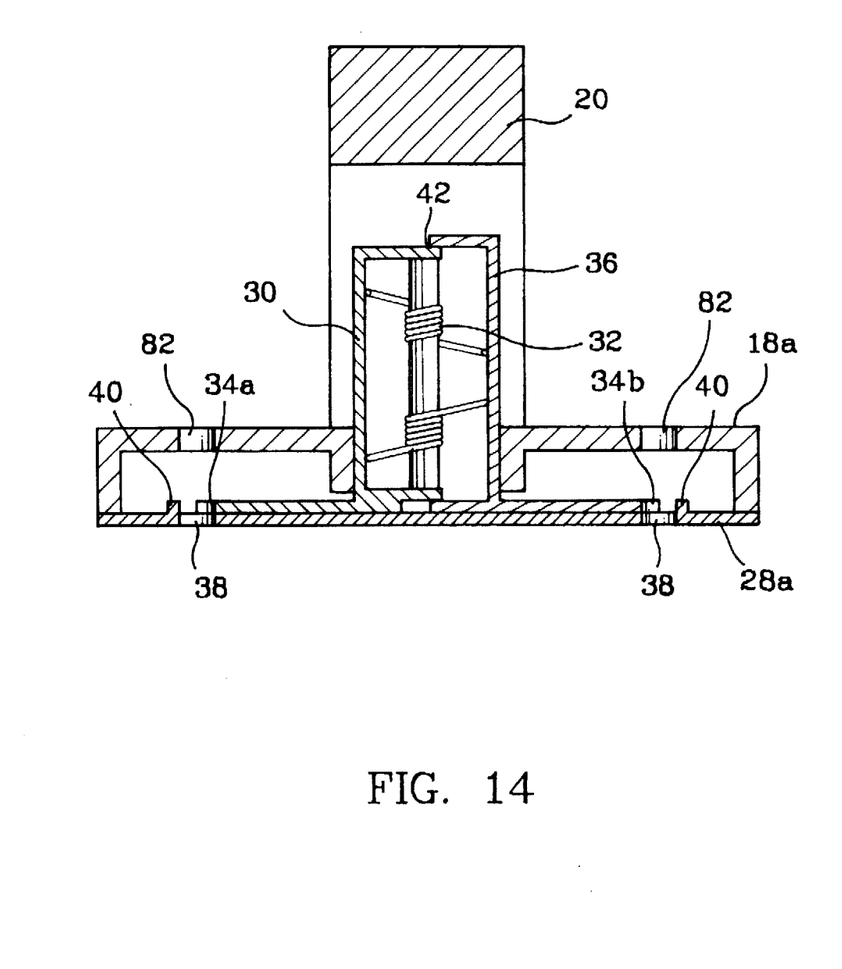
FIG. 14 is a sectional view taken along A—A line of FIG. 12, which shows the combination aspect of the multiple-test-bar access device of the second embodiment.
Figure 15:
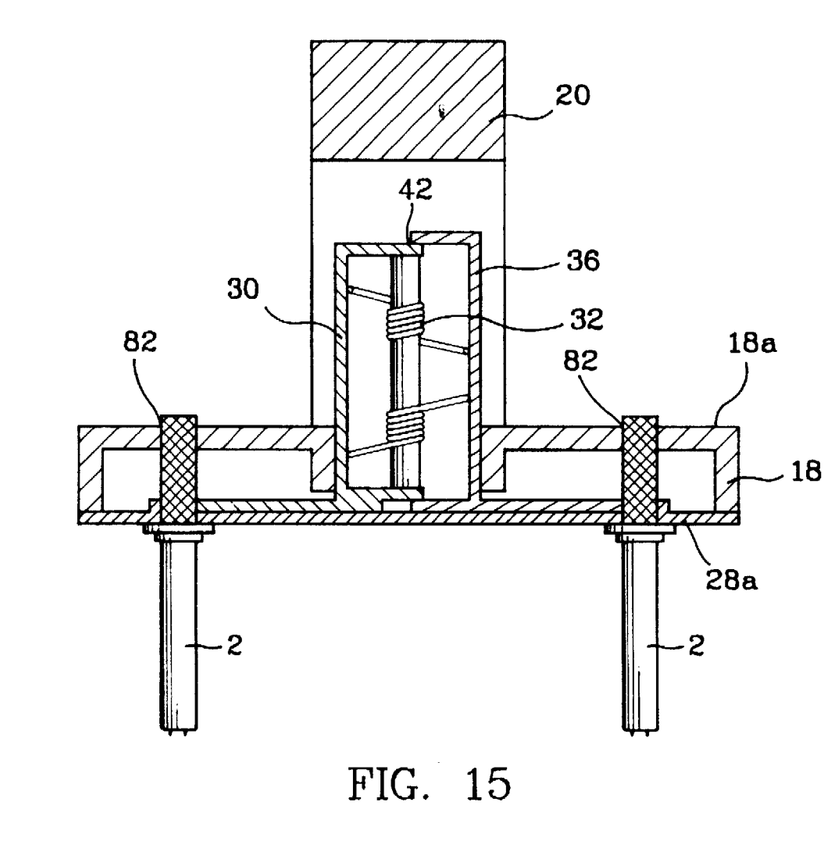
FIG. 15 is a sectional view similar to FIG. 14, in which multiple skin puncture test device (at least two) being held by the multiple-test-bar access device of the second embodiment is shown.

Referring again to FIG. 10, the outer panel (28) is placed to cover the bottom opening (23) and abut both of the first clamping plate (24) and the second clamping plate (26), wherein the holes of the panel (28) each are located to correspond to the semicircular-shaped cuts (34a) (34b), which will therefore correspondingly cooperate with the arcuate ridges (40) which are furnished at the outer edges of the holes (40) respectively to form multiple gripping holes therebetween, which each are formed coaxial with their corresponding holes of the outer panel (28). In normal state, the diameter of each gripping hole is somewhat smaller than that of a skin test bar. In use, when applying a force onto the switch portion (42), the first clamping plate (24) and the second clamping plate (26) will be moved toward each other so that all the gripping holes will get larger simultaneously to accommodate multiple the skin test bars simultaneously; when releasing the applying force, the spring means (32) enables the first clamping plate (24) and second clamping plate (26) to clamp the multiple skin test bars by means of semicircular-circular shaped cuts (34a) (34b) and their cooperating arcuate ridges (40). Accordingly, the simultaneous gripping of multiple skin test bars for a skin allergic test can be achieved (referring to FIG. 11).

More further, another embodiment regarding a multiple-test-bar access device is introduced herein for the same purpose as the above-described multiple-test-bar access device. As shown in FIGS. 12–15, this embodiment has a similar structure with the above-described multiple-test-bar device, except that the main frame (84) which has two longitudinal sides (80a)(80b) of a wave-like configuration and two parallel rows of frame holes (82) corresponding to the holes (38) of the outer panel (28a), and the outer panel (18a) which forms with two wave-like edges (100a)(100b) corresponding to the wave-like sides (80a)(80b) so as to be adaptable to the main frame. As shown in the figures, the finger grip of the skin puncture test bar may pass through the holes (38) of the outer panel (28a) into the frame holes (82) of the main frame. Such a feature will allow the user to make sure whether the skin puncture test bar is pressed on the test skin surface of a patient properly or not, by checking the contact condition of the multiple-test-bar access device through the adjacent space (102) between the individual waves.

Figure 16A:
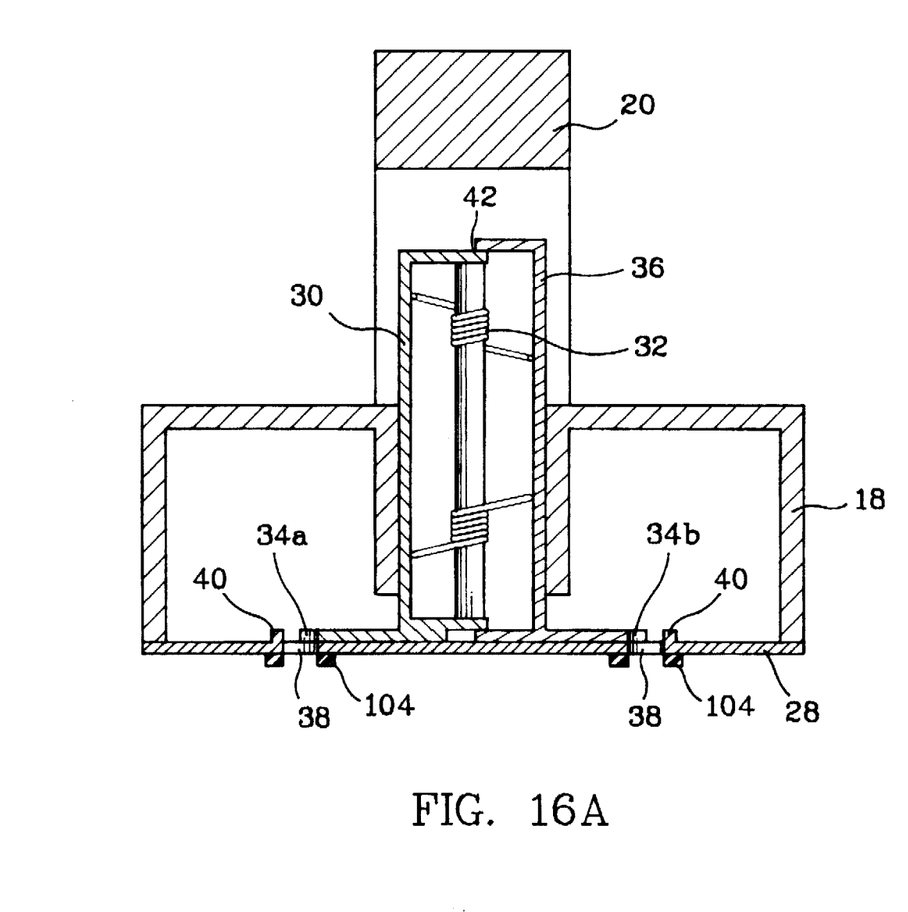
FIG. 16A show a multiple-test-bar access device to be attached with projections of resilient material around the hole of the outer panel.
Figure 16B:
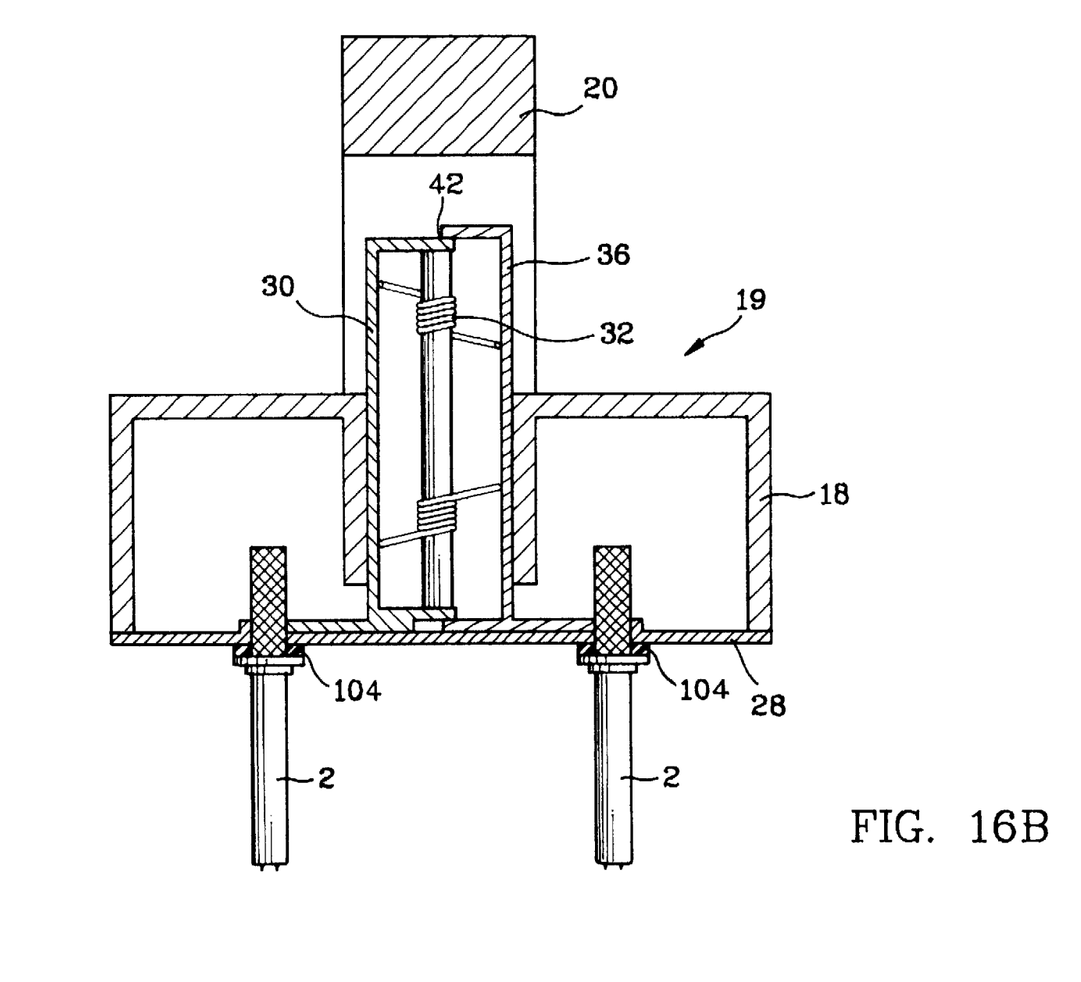
FIG. 16B show the multiple-test-bar access device having the projections of resilient material to be loaded with the skin puncture test bar of this invention.

Still more further, as shown in FIG. 16 A and 16B, in any one of the above-mentioned multiple-test-bars, projections of resilient material (104) may be attached to the outer panel around each hole (38) of the outer panel for providing the multiple-test-bar access device with resilience required in a skin allergic test.

Figure 17:
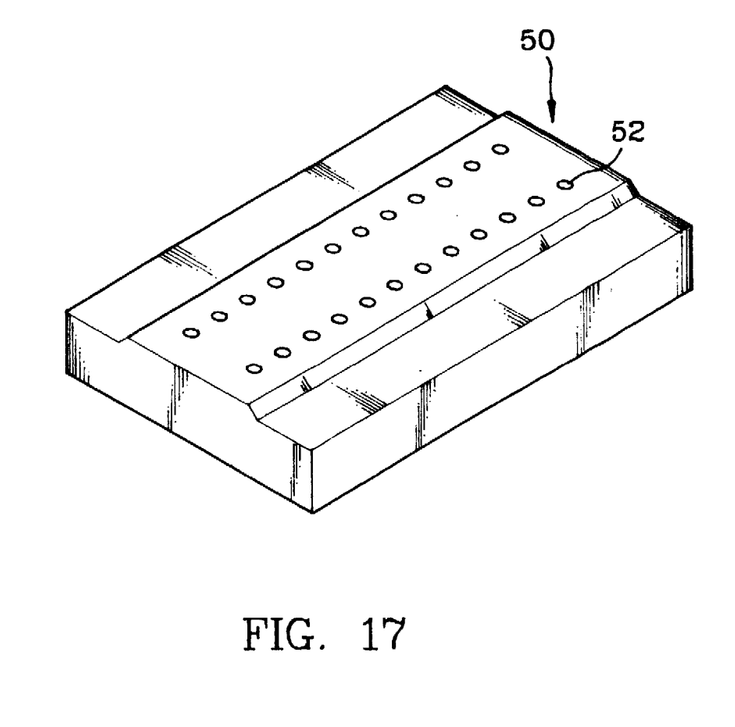
FIG. 17 is perspective view of a tray which is specially designed for cooperating the multiple-test-bar access device of this invention.

For making the multiple-test-bar access device (19) of the present invention more effective and useful, a specially-designed tray(50) is introduced herein in cooperation with the device. Please refer to FIG. 17, the tray (50) is formed with two parallel rows of tray holes (52) for holding a plurality of antigen-containing cup (9). The two parallel rows of tray holes (52) are aligned to correspond to the gripping holes which is formed by the semicircular-circular shaped cuts and the cooperating arcuate ridges, as well as the holes (38) of the outer panel (28). Accordingly, all the multiple skin puncture test bars can be directly taken from the antigen-containing cups immediately which are already held in the tray holes of the tray (50) for conducting a skin allergic test in which various specific kinds of antigen solution are required.

Figure 18:
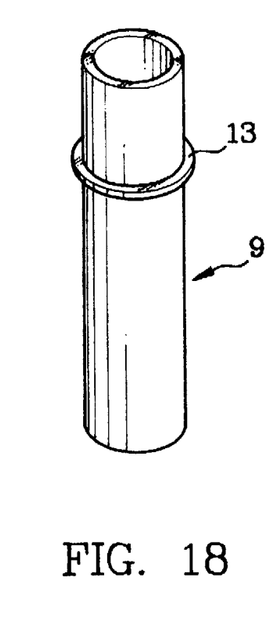
FIG. 18 shows an improved aspect of an antigen-containing cup of the present invention, the outer surface of which is furnished with a ring which is viewed as a mark for indicating the upper limit of the antigen-solution cup.

Referring to FIG. 18, the antigen-containing cup (19) as described above can be further furnished with a ring (13) on the outer surface thereof, which is viewed as a mark for indicating the upper limit of the antigen-containing cup in order to avoid the overflowing of the antigen solution when bringing the skin puncture test bar into the cup.

The improved skin puncture test bar (2), the multiple-test-bar access device (19), the tray (50) and the antigen-containing cup (9) of the present invention may be combined into a skin allergic assembly, which will be a more powerful and effective tool for a skin allergic test. In operating such a assembly, if only one specific antigen solution is required, then the skin puncture test bar (2) of this invention will just make it. On the other condition, if a skin allergic test in which various kinds of specific antigen solution are required is under a consideration, then the multiple-test-bar access device (19) will give much assistance to the skin allergic test. Regarding the skin allergic test assembly, when conducting a skin allergic test, the antigen-containing cups each are filled with various specific kinds of antigen solution respectively, then multiple unused sterile skin puncture test bars (2) of the present invention each may be put into a antigen-containing cup on a tray, and finally the multiple-test-bar access device may be employed to take all the multiple skin puncture test bars at a clamp by the procedures as described above. Simply by forcing the multiple-test-bar access device directly onto the desired test site of a patient, the skin allergic test will be completed at a press. After finishing the skin allergic test, the user may press the switch portion of the multiple-test-bar access device once again to throw the used test bars away.

Although the description above contains many references to specific versions and aspects of the invention, this circumstance should not be construed as limiting the scope of the invention but as merely providing illustrations of some of the presently preferred embodiments of this invention. For example, the concave surface of the puncture test bar may be a flat recessed surface; the semicircular-shaped cut can be furnished with an arcuate ridge to cooperate the arcuate ridge of the outer panel for improving the gripping tightness. Therefore, the scope of this invention should be determined by the appended claims and their legal equivalents, rather than by the examples given in the descriptions above.

I claim:

1. In a skin puncture test bar comprising a finger grip, an elongated stem extending therefrom, and a plurality of punctures provided at an end of said elongate stem, the improvement of said skin allergic test bar comprising:

the end of said elongate stem being formed with a concave surface on which said plurality of punctures are provided, said plurality of punctures extending directly from said concave surface substantially parallel to said elongated stem to project out of the outer edge of said concave surface at a predetermined length less than the thickness of the human epidermis layer so that the penetration made by said skin puncture test bar will have a limited penetration depth due to an outer edge of said concave surface which acts as a stop, therefore said punctures will make a limited penetration to avoid the penetration through of the epidermis layer of the skin of a patient and provide an adequate amount of antigen solution to a test site of the patient.

2. The skin puncture test bar of claim 1 wherein the improvement further comprising:

a cover furnished between said finger grip and said elongated stem so as to prevent an antigen-containing cup from being contaminated when said skin puncture test bar is mated with said antigen-containing cup.

3. A multiple-test-bar access device for holding multiple skin puncture test bars simultaneously, said device comprising:

a main frame;

a first clamping plate formed with a plurality of semicircular-shaped cuts along a longitudinal edges thereof;

a second clamping plate formed with a plurality of semicircular-shaped cuts along a longitudinal edge thereof, said second plate adapted to mate with said first clamping plate and adapted to assemble into said main frame together with said first clamping plate;

an outer panel placed to abut both of said first clamping plate and said second clamping plate and having two parallel rows of holes formed thereon, each hole corresponding to each said semicircular-shaped cut of said first and second clamping plates and each hole furnished with an arcuate ridge at its outer edge for cooperating each said semicircular-shaped cut correspondingly; and means for providing an elastic force to said first clamping plate and said second clamping plate respectively for gripping multiple skin puncture test bars between said semicircular-shaped cuts and said arcuate ridges.

4. The multiple-test-bar access device of claim 3 wherein said main frame having two wave-like sides and two parallel rows of frame holes, said outer panel having two wave-like edges corresponding to said wave-like sides to be adaptable to said main frame.

5. The multiple-test-bar access device of claim 3 wherein a plurality of projections of resilient material attached to said outer panel around the circumference of each said hole thereof.

6. A multiple-test-bar access device for holding multiple skin puncture test bars simultaneously, said device comprising:

a main frame having a handle for being held by a user's fingers, a slot, and a bottom opening;

a first clamping plate formed with a plurality of semicircular-shaped cuts along a longitudinal edge thereof and furnished with a box at the other longitudinal edge thereof for housing a spring means therein, the height of said box being greater than the depth of said slot of said main frame;

a second clamping plate formed with a plurality of semicircular-shaped cuts along a longitudinal edge thereof and furnished with a mating box at the other longitudinal edge thereof for mating with said box, the height of said mating box being greater than the depth of said slot of said main frame, said box and said mating box being assembled together to form an elastic and relatively-movable integral enclosure in which said spring is housed, said enclosure being assembled into said slot of said main frame and extending out of said slot to form a switch portion thereabove, so that said spring means can exert an exert force on each inner surface of said box and said mating box to have said first clamping plate and said second clamping plate capable of providing an outward force, and said box and said mating box can be moved toward each other as pressing said enclosure; and an outer panel formed with two parallel rows of holes thereon, each hole corresponding to each said semicircular-shaped cut of said first and second clamping plates and each hole furnished with an arcuate ridge at its outer edge for cooperating with each said semicircular-shaped cut correspondingly, said outer panel placed to cover said bottom opening of said main frame and abut both of said first clamping plate and said second clamping plate where each said hole of said outer panel is located to correspond to each said semicircular-shaped cut of said first and second clamping plate so that each said arcuate ridge furnished at its hole will cooperate with each said semicircular-shaped cut correspondingly to form multiple gripping holes therebetween, each gripping hole being coaxial with its corresponding hole of said outer panel, the diameter of each said gripping hole being somewhat smaller than that of a skin puncture test bar in normal state; when pressing said switch portion, said first clamping plate and said second clamping plate will move toward each other, thereby making all the gripping holes get larger simultaneously so as to accommodate said multiple skin puncture test bars simultaneously; when releasing the pressing force, said spring means will cause said first clamping plate and said second clamping plate to enable said multiple skin puncture test bars by means of said arcuate ridges and said semicircular-circular shaped cuts so as to take said multiple skin puncture test bars simultaneously.

* * * * *